US007550479B2

United States Patent
Orme et al.

(10) Patent No.: US 7,550,479 B2
(45) Date of Patent: Jun. 23, 2009

(54) MODIFIED PICTET-SPENGLER REACTION AND PRODUCTS PREPARED THEREFROM

(75) Inventors: Mark W. Orme, Seattle, WA (US); Michael J. Martinelli, Thousand Oaks, CA (US); Christopher W. Doecke, Indianapolis, IN (US); Joseph M. Pawlak, Indianapolis, IN (US); Erik C. Chelius, Innishannon (IE)

(73) Assignee: Lilly ICOS LLC, Wilmington, DE (US)

( * ) Notice: Subject to any disclaimer, the term of this patent is extended or adjusted under 35 U.S.C. 154(b) by 492 days.

(21) Appl. No.: 10/521,393

(22) PCT Filed: Jul. 14, 2003

(86) PCT No.: PCT/US03/22039

§ 371 (c)(1), (2), (4) Date: Jul. 21, 2005

(87) PCT Pub. No.: WO2004/011463

PCT Pub. Date: Feb. 5, 2004

(65) Prior Publication Data

US 2006/0004203 A1 Jan. 5, 2006

Related U.S. Application Data

(60) Provisional application No. 60/460,161, filed on Apr. 3, 2003, provisional application No. 60/400,386, filed on Jul. 31, 2002.

(51) Int. Cl.
A01N 43/42 (2006.01)
A61K 31/44 (2006.01)

(52) U.S. Cl. .................................................. 514/291

(58) Field of Classification Search .................. None
See application file for complete search history.

(56) References Cited

U.S. PATENT DOCUMENTS 5,859,006 A    1/1999  Daugan
6,878,711 B2 * 4/2005  Orme et al. ................. 514/250
7,098,209 B2 * 8/2006  Orme et al. ................. 514/250

FOREIGN PATENT DOCUMENTS

WO    WO2002036593    * 5/2002

OTHER PUBLICATIONS

P.D. Bailey et al., *J. Chem. Soc. Perkin Trans. 1*, 431-39 (1993).
A. Madrigal et al., *Tetrahedron: Asymmetry*, 11, 3515-26 (2000).
A. Ishida et al., *Chem. Pharm. Bull.*, vol. 3, 3237-49 (1985).
H. Wang et al., *Organic Letters*, vol. 1, No. 10, 1647-49 (1999).
P.D. Bailey et al., *Tetrahedron Letters*, vol. 28, No. 25, 2879-82 (1987).
P.D. Bailey et al., *Tetrahedron Letters*, vol. 35, No. 21, 3587-88 (1994).
P.D. Bailey et al., *J. Chem. Soc., Chem. Commun.*, 1507-09 (1985).
P.D. Bailey et al., *J. Chem. Soc. Perkin Trans. 1*, 739-45 (1988).
P.D. Bailey et al., *Tetrahedron Letters*, vol. 28, No. 43, 5177-80 (1987).
P.D. Bailey et al., *J. Chem. Soc. Perkin Trans. 1*, 451-58 (1993).
P.D. Bailey et al., *Tetrahedron Letters*, vol. 32, No. 31, 3895-98 (1991).
P.D. Bailey et al., *J. Chem. Soc. Perkin Trans. 1*, 441-49 (1993).
P.D. Bailey et al., *Tetrahedron Letters*, vol. 35, No. 21, 3585-86 (1994).
P.D. Bailey et al., *J. Chem. Soc. Perkin Trans. 1*, 1209-14 (1997).
P.D. Bailey et al., *Chem. Commun.*, 1479-80 (1996).
P.D. Bailey, *Tetrahedron Letters*, vol. 28, No. 43, 5181-84 (1987).
K.M. Czerwinski et al., *Tetrahedron Letters*, vol. 33, No. 33, 4721-24 (1992).
F. Ungemach et al., *J. Org. Chem.*, 164-68 (1981).
W-M. Dai et al., *Tetrahedron Letters*, vol. 37, No. 33, 5971-74 (1996).
L. Deng et al., *Tetrahedron Letters*, vol. 32, No. 2, 175-78 (1991).
M.L. Trudell et al., *Tetrahedron*, vol. 48, No. 10, 1805-22 (1992).
C. Gremmen et al., *Tetrahedron Letters*, 39, 1441-44 (1998).
P. Zhang et al., *Tetrahedron Letters*, vol. 36, No. 39, 6999-7002 (1995).
A. Ganesan, Recent Studies in Total and Combinatorial Synthesis, Department of Chemistry, University of Southampton, Undated.

* cited by examiner

*Primary Examiner*—James O Wilson
*Assistant Examiner*—Jeffrey H Murray
(74) *Attorney, Agent, or Firm*—Dan L. Wood; James J. Napoli

(57) ABSTRACT

A method of introducing a second stereogenic center into a tetrahydro-β-carboline have two stereogenic centers using a modified Pictet-Spengler reaction is disclosed. The method provides a desired cis- or trans-isomer in high yield and purity, and in short processes times.

5 Claims, No Drawings

MODIFIED PICTET-SPENGLER REACTION AND PRODUCTS PREPARED THEREFROM

CROSS-REFERENCE TO RELATED APPLICATIONS

This is the U.S. national phase application of International Application No. PCT/US2003/022039, filed Jul. 14, 2003, which claims the benefit of U.S. provisional patent application Ser. No. 60/460,161, filed Apr. 3, 2003 and U.S. provisional patent application Ser. No. 60/400,386, filed Jul. 31, 2002.

FIELD OF THE INVENTION

The present invention relates to a modified Pictet-Spengler reaction for introducing a second stereogenic center into a compound. More particularly, the present invention relates to a modified Pictet-Spengler reaction that provides a desired cis- or trans-diastereomer of a polycyclic compound having two stereogenic centers, in high yield and high purity.

BACKGROUND OF THE INVENTION

Compounds that exhibit biological activity typically contain at least one asymmetric carbon atom, i.e., at least one choral center. A particular stereoisomer of such a compound usually exhibits excellent biological activity, whereas the other stereoisomers exhibit no or little biological activity. Accordingly, investigators strive to synthesize the biologically active stereoisomer, while minimizing or eliminating synthesis of the inactive or less active stereoisomer.

Stereochemical purity is important in the pharmaceutical field, where many of the most often prescribed drugs exhibit chirality. For example, the L-enantiomer of the β-adrenergic blocking agent, propranolol, is known to be 100 times more potent than its D-enantiomer. Additionally, optical purity is important in the pharmaceutical field because certain stereoisomers impart a deleterious effect, rather than an advantageous or inert effect. For example, it is believed that the D-enantiomer of thalidomide is a safe and effective sedative when prescribed for the control of morning sickness during pregnancy, whereas its corresponding L-enantiomer is believed to be a potent teratogen.

A stereoselective synthesis, therefore, permits the preparation of a more useful drug product. For example, the administered dose of a drug can be reduced because only the active stereoisomer is administered to at individual, as opposed to a mixture which contains a large amount of inactive stereoisomer. This reduced dose of active stereoisomer also reduces adverse side effects compared to a dose containing a mixture of stereoisomers. In addition, a stereoselective synthesis is more economical because a step of separating the desired stereoisomer from the undesired stereoisomer is simplified or eliminated, and raw material wastes and costs are decreased because reactants are not consumed in the synthesis of undesired stereoisomers.

Many biologically active compounds contain two asymmetric carbon atoms, i.e., two stereogenic centers, wherein each asymmetric carbon atom is a member of a ring system and each is bonded to a hydrogen atom and to a substituent different from a hydrogen atom. The nonhydrogen substituents of the asymmetric carbon atoms therefore can be in a cis or a trans configuration. A particularly difficult problem encountered in the synthesis of such biologically active compounds is the high yield and high purity preparation of a particular stereoisomer, i.e., the desired diastereomer, wherein the nonhydrogen substituents of the asymmetric carbon atoms are in the cis configuration, or the trans configuration, depending upon which diastereomer is the more biologically active.

For such compounds, it is necessary to provide a synthetic pathway that provides each stereogenic center of correct stereochemistry, and thereby yield the desired diastereomer. The synthetic pathway also should provide a high yield of the desired diastereomer in as few steps as possible, with a minimum of diastereomer separation and purification.

For example, U.S. Pat. No. 5,859,006, incorporated herein by reference, discloses the synthesis of (6R, 12aR)-2,3,6,7,12,12a-hexahydro-2-methyl-6-(3,4-methylenedioxyphenyl)-pyrazino-[2',1':6,1]pyrido[3,4-b]indole-1,4-dione having a structure (I):

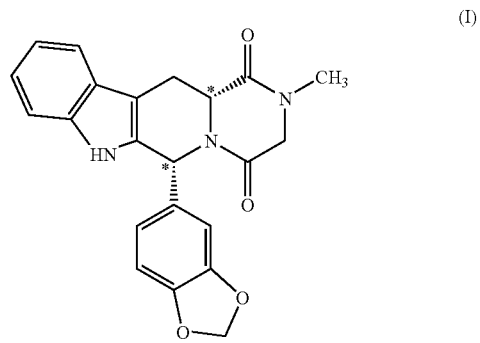

Compound (I) has two asymmetric carbon atoms, each denoted by an asterisk, wherein the nonhydrogen substituents of the asymmetric-carbon atoms are in the cis configuration. Compound (I) can be prepared by the two synthetic pathways disclosed in U.S. Pat. No. 5,859,006. Compound (I) is a potent and selective inhibitor of the phosphodiesterase enzyme PDE5, and has various therapeutic uses, for example, the treatment of male erectile dysfunction.

The first synthetic pathway (A), from D-tryptophan, has few steps, but the yield of the desired diastereomer (i.e., Compound II) is poor and requires a separation step from the trans-stereo-isomer (Compound IIa). Pathway (A) also utilizes the highly corrosive trifluoroacetic acid (i.e., TFA or $CF_3CO_2H$). The key step in pathway A is a classic Pictet-Spengler reaction using D-tryptophan methyl ester and piperonal to yield substituted tetrahydro-β-carboline Compounds (II) and (IIa). The second pathway (B) provides a better yield of the desired Compound I, but requires numerous synthetic steps. In each synthetic pathway, the key intermediate in the synthesis of Compound (I) is Compound (II). Compound (I) then is synthesized from Compound (II) in two straightforward synthetic steps.

Pathway A

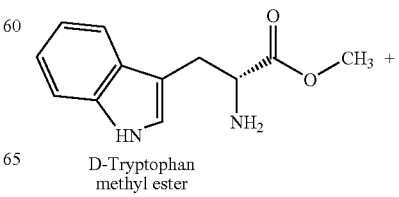

D-Tryptophan methyl ester

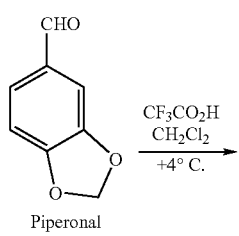
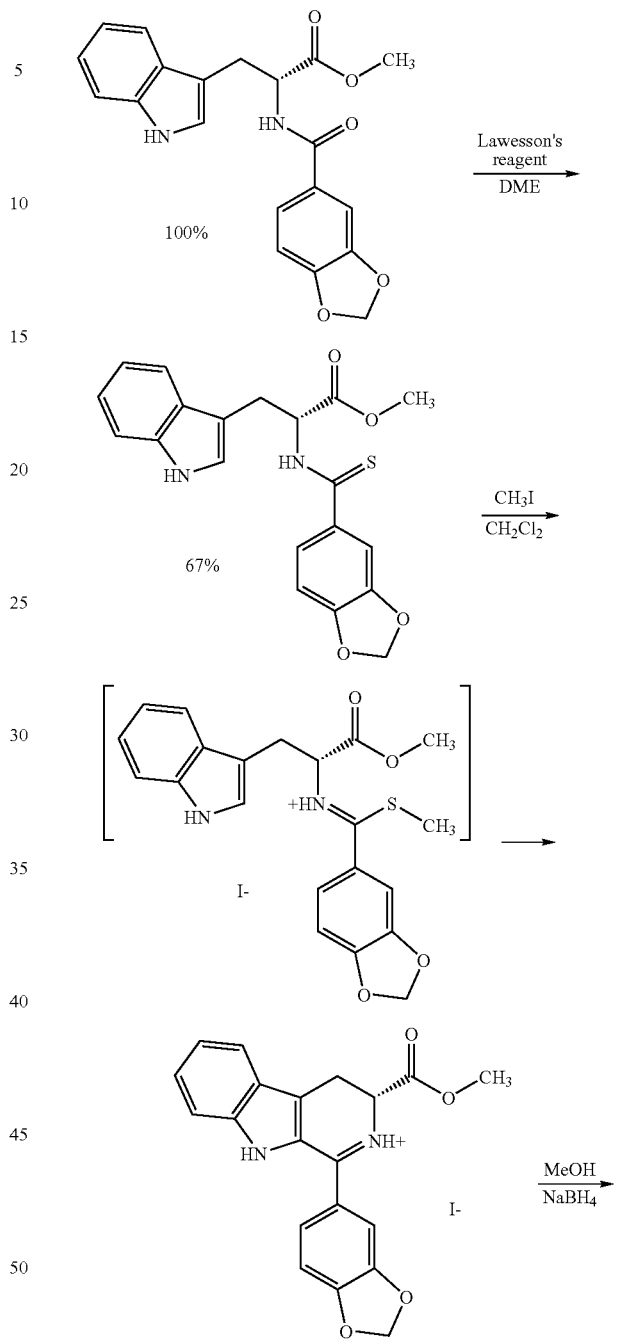
Pathway B
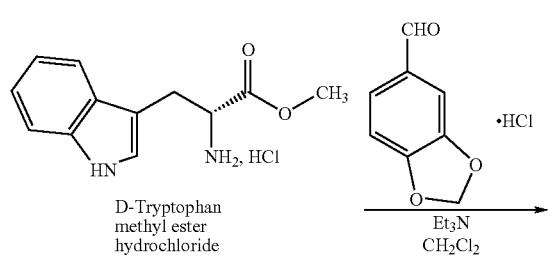

Pathway from Compound (II) to Compound (I)

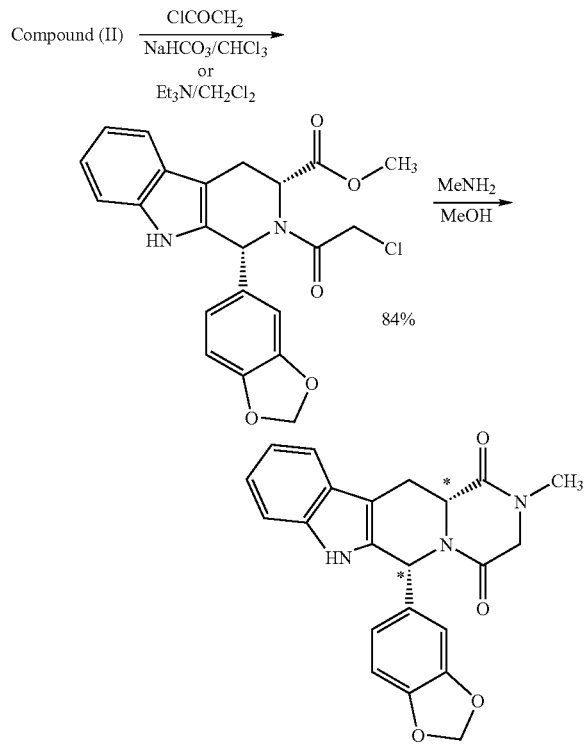

The overall yield of Compound (I) using synthetic pathway (A) or (B) is about 25% to about 30%.

Pathway (B) requires several synthetic steps, and, therefore, was considered inconvenient. A key step in the synthesis of Compound (I) is the preparation of Compound (II) in the shorter synthetic pathway (A). The preparation of Compound (II) in pathway (A) utilizes a Pictet-Spengler cyclization between D-tryptophan methyl ester and piperonal in dichloromethane ($CH_2Cl_2$) with two equivalents of trifluoroacetic acid at 4° C. which provides, after five days, a mixture of two diastereoisomers, i.e., the desired cis-isomer tetrahydro-β-carboline Compound (II) ((1R, 3R)) and the undesired trans-isomer tetrahydro-β-carboline Compound (IIa) ((1S, 3R)) in a ratio of about 60/40. From this mixture, the pure cis-isomer (i.e., Compound (II)) can be obtained by fractional crystallization in a 42% yield (ee>99% (chiral HPLC)).

The Pictet-Spengler reaction is a direct method of providing the tetrahydro-β-carboline ring system that is present in Compound (I). In general, the Pictet-Spengler reaction utilizes a tryptophan ester and an aldehyde to yield a mixture of the cis-1,3- and trans-1,3-tetrahydro-β-carbolines illustrated below. $R^2$ typically is $C_{1-4}$alkyl and $R^1$ can be aliphatic or aromatic, for example, see U.S. Pat. Nos. 5,859,006 and 5,981,527, each incorporated herein by reference.

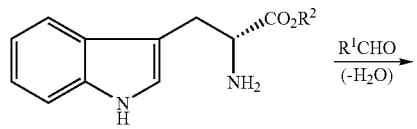

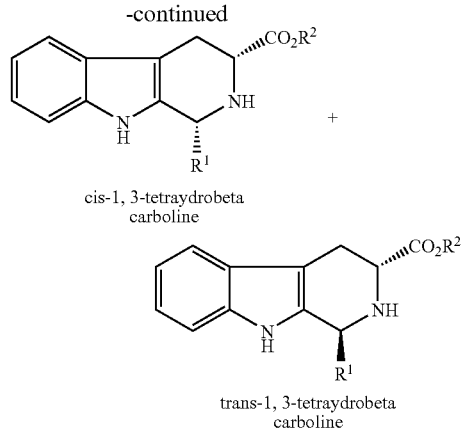

cis-1, 3-tetraydrobeta carboline trans-1, 3-tetraydrobeta carboline

It would be an important advance in the art to provide a modified Pictet-Spengler cyclization reaction that substantially improves the disastereoselectivity of the reaction. In particular, it would be an advance in the art to improve pathway A, which utilizes the Pictet-Spengler reaction between commercially available D-tryptophan methyl ester and piperonal, or other aliphatic or aromatic aldehyde, in a straightforward method to prepare enantiomerically pure Compound (II), or similar tetrahydro-β-carboline, and that overcomes the disadvantages of the classic Pictet-Spengler reaction, such as use of TFA, long reaction times, and difficult product separations.

SUMMARY OF THE INVENTION

The present invention is directed to a method of preparing a desired diastereomer, i.e., cis or trans, of a polycyclic compound having two asymmetric ring carbon atoms. More particularly, the present invention is directed to a method of preparing a desired diastereomer of a tetrahydro-β-carboline compound having two asymmetric carbon atoms utilizing a modified Pictet-Spengler reaction.

Prior investigators attempted to prepare a desired diastereomer of a polycyclic ring system containing two asymmetric ring carbon atoms by performing a Pictet-Spengler cyclization reaction. These attempts generally were limited in success because the reaction was performed in a corrosive medium, led to mixtures of diastereomers that adversely affected reaction yield, and required several days to perform. The present method provides the desired diastereomer in good yield and short reaction times, and avoids the use of TFA.

More particularly, the present invention is directed to a method of preparing a desired diastereomer of a tetrahydro-β-carboline compound having two asymmetric carbons utilizing a modified Pictet-Spengler cyclization reaction wherein the reaction is performed using a solvent in which only one of the diastereomers is soluble. In preferred embodiments, the desired diastereomer is insoluble in the solvent, and undesired diastereomer is soluble.

Another aspect of the present invention is to increase the yield of the desired diastereomer by allowing the undesired diastereomer to equilibrate in solution to provide additional desired diastereomer that precipitates from solution, and thereby increase the yield of the desired diastereomer at the expense of the undesired diastereomer.

These and other aspects and novel features of the present invention will become apparent from the following detailed description of the preferred embodiments.

DETAILED DESCRIPTION OF THE PREFERRED EMBODIMENTS

The present invention is directed to a method of preparing a desired diastereomer of a polycyclic compound having two asymmetric carbon atoms as members of a ring system. The method utilizes an improved Pictet-Spengler reaction that provides a desired tetrahydro-β-carboline diastereomer in high yield, high purity, and in a short process time. The improved Pictet-Spengler reaction also avoids the use of TFA in the reaction.

Although the synthesis of Compounds (I) and (II) are particularly discussed herein, the present method is not limited to these compounds. The present method also can be used to synthesize the desired diastereomer of other tetrahydro-β-carbolines by a judicious selection of starting tryptophan ester, e.g., the D- or L-form, the starting aldehyde, and the reaction solvents utilized in the present modified Pictet-Spengler cyclization reaction.

Typically, the Pictet-Spengler reaction proceeds through generation of an imine under neutral conditions, then effecting cyclization using trifluoroacetic acid (TFA) in dichloromethane ($CH_2Cl_2$) at a low temperature (4° C.). In addition to starting with an imine, N-substitution of the tryptophan amino (—$NH_2$) group often is used to provide a cis-diastereomer. The Pictet-Spengler reaction disclosed in U.S. Pat. No. 5,859,006 uses such conditions. As discussed above, the standard Pictet-Spengler reaction has the disadvantages of a long cycle time, a low yield of the desired cis-diastereomer, and use of the corrosive TFA.

The present invention overcomes problems associated with the classic Pictet-Spengler reaction, e.g., improves the yield and purity of the desired diastereomer, and utilizes a more facile synthetic route. In particular, the present invention is directed to a simplified Pictet-Spengler reaction for generating a second ring stereogenic center, wherein the desired cis- or trans-diastereomer can be prepared in high yield and purity by performing the reaction in a solvent in which the desired diastereomer is insoluble and the undesired diastereomer is soluble. The modified Pictet-Spengler reaction of the present invention also utilizes an N-unsubstituted starting material, e.g., tryptophan, as the hydrochloride salt, and eliminates the use of TFA. The elimination of TFA from the reaction has substantial advantages, including improved isolation/identification of the tryptophan methyl hydrochloride and overcoming the corrosive properties of TFA.

The selection of a proper solvent for use in the present modified Pictet-Spengler reaction is well within the skill of persons in the art. For example, in the preparation of Compound (II) by the Pictet-Spengler cyclization reaction, isopropyl alcohol was found to solubilize the undesired trans-diastereomer, whereas the desired cis-diastereomer precipitated from the reaction mixture. In addition, the solubilized trans-diastereomer is in dynamic equilibrium with the desired cis-diastereomer. Accordingly, as the cis-diastereomer Compound (II) is formed in solution and immediately precipitates, its concentration is lowered relative to the remaining trans-diastereomer Compound (IIa), thereby providing a concentration differential that forces the equilibrium to provide additional cis-diastereomer. This continuous driving of the reaction increases both the yield and purity of the desired cis-diastereomer.

In particular, the present invention utilizes a modified Pictet-Spengler cyclization reaction to form a tetrahydro-β-carboline ring system having two stereogenic centers. The reaction is performed in a solvent wherein the desired diastereomer is soluble at reflux temperature or below, and the undesired diastereomer is insoluble at reflux temperature or below. This solubility difference allows a fast and easy separation of the desired diastereomer from the undesired diastereomer. Furthermore, the dynamic cis-trans equilibrium in solution allows a more complete conversion of the starting materials to the desired diastereomer, and a more complete separation of the desired diastereomer from the undesired diastereomer. Accordingly, another advantage of the present invention is a decrease in costs attributed to a more efficient use of reagents.

As previously stated, the selection of a reaction solvent having the requisite solubility properties is within the ability of a person skilled in the art. The selection merely requires determination of the solubility of each diastereomer in a particular solvent, and a solvent selection that meets the above-described solubility/insolubility parameters for the two diastereomers.

The following is a nonlimiting example of the present invention, illustrating the synthesis of Compound (II) by the modified Pictet-Spengler reaction (Step 2), and the subsequent synthesis of Compound (I) from Compound (II) (Steps 3 and 4).

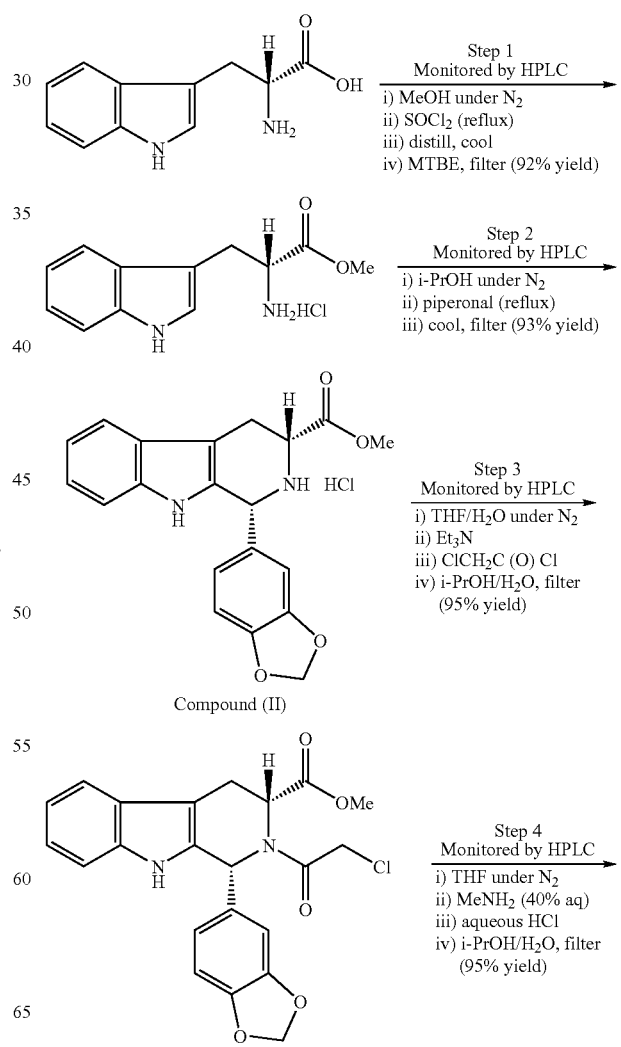

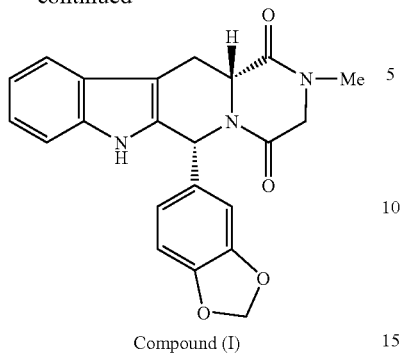

Compound (I)

In general, the synthesis of compound (I) using the method of the present invention involves a four-step synthetic pathway. The first step is an esterification in methanol (MeOH) using thionyl chloride (SOCl$_2$) under reflux. The product is crystallized and isolated by filtration. The second step involves the present novel and simplified variation of the Pictet-Spengler reaction, wherein D-tryptophan methyl ester hydrochloride is admixed with piperonal in isopropyl alcohol (i-PrOH) and heated under reflux to form a mixture of diastereomeric adducts. Because the desired cis-diastereomer (Compound (II)) is substantially insoluble in isopropyl alcohol at reflux temperature and below, the cis-diastereomer crystallizes from solution leaving a dynamic cis-trans equilibrium in solution. As the cis-diastereomer precipitates from the isopropyl alcohol, the equilibrium is driven towards the cis-diastereomer until the concentration of the cis-diastereomer is sufficiently low to remain in solution. The desired diastereomer is isolated in greater than 90% yield by crystallization and filtration.

The third step involves an aqueous tetrahydrofuran (THF) acylation of the amino (NH$_2$) moiety of Compound (II), followed by crystallization and filtration. Ring closure with methylamine (MeNH$_2$) completes the ring-forming sequence. After solvent exchange, the product is crystallized from aqueous isopropyl alcohol or other suitable solvent, and filtration provides Compound (I) in an overall yield of about 77%.

In general, the present modified Pictet-Spengler reaction can be used to prepare the desired diastereomer of tetrahydro-β-carboline-based compounds without limitation. For example, the present modified Pictet-Spengler reaction can be used to synthesize the desired diastereomer of classes of compounds disclosed in U.S. Pat. Nos. 5,859,006; 5,981,527; 6,001,847, WO 02/28859, WO 02/28865, WO 02/10166, WO 02/36593, WO 01/94345, WO 02/00658, WO 02/00657, WO 02/38563, WO 01/94347, WO 02/94345, WO 02/00656, PCT/US01/49393, PCT/US02/13719, PCT/US02/00017, PCT/US02/10367, PCT/US02/13703, PCT/US02/11791, and PCT/US02/13897, each incorporated herein by reference, and other substituted tetrahydro-β-carbolines.

In addition to the preparation of tetrahydro-β-carboline diketo-piperazines, like Compound (I), the present method can be used to prepare tetrahydro-β-carboline hydantoins (III) of desired stereochemistry by reacting a compound such as Compound (II) with an isocyanate having a formula R$^4$NCO, wherein R$^4$ is aliphatic or aromatic. See U.S. Pat. No. 6,001,847, incorporated herein by reference.

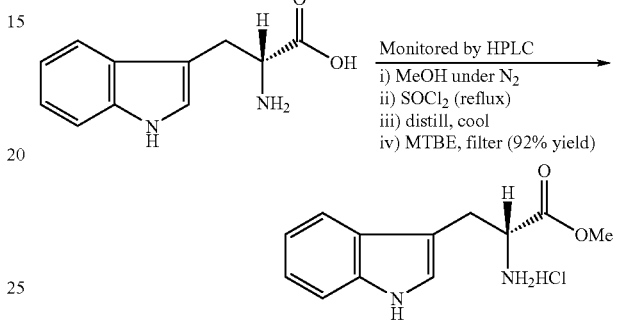

(III)

The following provides a detailed exemplary preparation of Compound (I) utilizing the method of the present invention.

Step 1

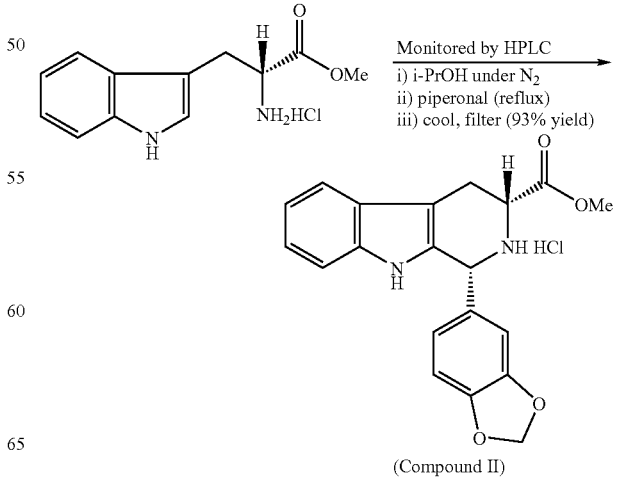

D-Tryptophan (50.0 kg, 245 mol) was Suspended in MeOH (270 L), then added to a prepared solution of SOCl$_2$ (67.0 kg, 563 mol) in MeOH (250 L) at ambient temperature under a nitrogen (N$_2$) atmosphere. The resulting solution was stirred at reflux for 1 to 2 hours, then MeOH was distilled from the reaction mixture to about 50% of original volume. Methyl t-butyl ether (MTBE) (350 L) was added, and the solution was cooled to 0° to 5° C., with continued stirring for 1 hour. The product was filtered, washed with cold MTBE (150 L), and dried in vacuum at 60° C. to yield 57.6 kg (92.4%) of D-tryptophan methyl ester hydrochloride. $^1$H NM (400 MHz DMSO) δ: 11.15 (1H, s), 8.70 (2H, exch.), 7.50 (1H, d, J=8.2 Hz), 7.35 (1H, d, J=8.2 Hz), 7.24 (1H, s), 7.08-7.05 (1H, m), 7.00-6.97 (1H, m), 4.18-4.16 (1H, m), 3.61 (3H, s), 3.36-3.25 (2H, m). HPLC Details: Column: SB-Phenyl 4.6×250 mm; Eluent: Isocratic 80% (H$_2$O+0.1% TFA)/20% ACN (acetonitrile); Temperature: 40° C.; Flow Rate=1 mL/min; UV Detection=285 nm; Injection Volume=20 μL; Diluent=1:1 ACN/H$_2$O; and Retention Time=10.0 min.

Step 2

D-Tryptophan methyl ester hydrochloride (50.0 kg, 196 mol) was suspended in isopropyl alcohol (500 L) and treated with piperonal (32.4 kg, 216 mol) at ambient temperature under an $N_2$ atmosphere. The mixture was stirred between 70° C. and reflux (82° C.) for 16 to 18 hours. At this time, the reaction mixture contained less than 3% Compound IIa. The reaction mixture then was cooled to 0° C., filtered, and washed with cold isopropyl alcohol (150 L). The product was dried under vacuum at less than 60° C. to yield 69.8 kg (92%) of cis-1-(1,3-benzodioxol-5-yl)-2,3,4,9-tetrahydro-1H-pyrido[3,4-b]indole-3-carboxylic acid methyl ester (Compound II)). $^1$H NMR (400 MHz DMSO) δ: 10.81 (1H, s), 10.67 (1H, exch.), 10.21 (1H, exch.), 7.52 (1H, d, J=8.0 Hz), 7.27 (1H, d, J=8.0 Hz), 7.11 (1H, m), 7.05-6.95 (4H, m), 6.08 (2H, s); 5.85 (1H, m), 4.71 (1H, m), 3.82 (3H, s), 3.39-3.23 (2H, m). HPLC Details: Column: SB-Phenyl 4.6×250 mm; ACN/(H$_2$O+0.1% TFA) gradient; Temperature: 40° C.; Flow Rate=1 mL/min; UV Det.=285 μm; Injection Volume=20 μL; Diluent=1:1 ACN/H$_2$O; Sample concentration: about 0.1 mg/mL; and Retention time=6.0 min.

In a preferred method of preparing Compound (II) by the present method, a small seed amount of Compound (II), i.e., about 0.05% to about 1%, and preferably about 0.05% to about 0.25%, based on the weight of D-tryptophan methyl ester hydrochloride, is added to the reaction mixture prior to heating. This seed amount induces crystallization of the cis-carboline Compound (II) in the reaction mixture.

When isopropyl alcohol is used as the solvent, it is preferred that the alcohol is anhydrous, e.g., 0.1% water or less, by weight, because appreciable amounts of water can adversely affect the rate of reaction. It is especially preferred that the isopropyl alcohol is essentially free of acetone, i.e., contains 0.3% acetone or less, by weight, to avoid formation of an undesired byproduct.

Use of a higher-boiling solvent (e.g. n-propanol, toluene, dimethylformamide, acetonitrile, or acetic acid) leads to faster reaction times with comparable product yield and purity.

Other solvents useful in the preparation of Compound (II) using a Pictet-Spengler reaction (Step 2) of the present invention include, but are not limited to, aromatic solvents (e.g., toluene, benzene, or xylene), a nitrile (e.g., acetonitrile or propionitrile), an ester (e.g., ethyl acetate), an alcohol (e.g., a propanol or butanol), an ether (e.g., THF, MTBE, or dioxane), an aliphatic hydrocarbon (e.g., hexane, heptane), an organic acid (e.g., acetic acid), mixtures thereof, and aqueous solutions thereof.

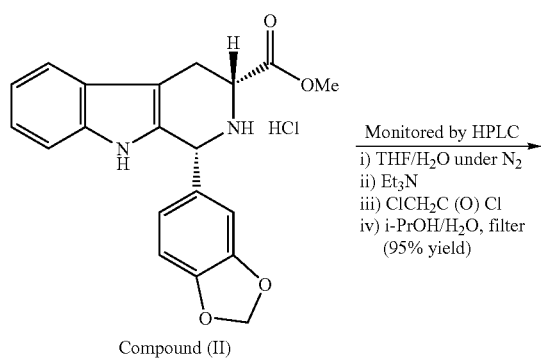

Compound (II)

Monitored by HPLC
i) THF/H$_2$O under N$_2$
ii) Et$_3$N
iii) ClCH$_2$C (O) Cl
iv) i-PrOH/H$_2$O, filter
(95% yield)

-continued

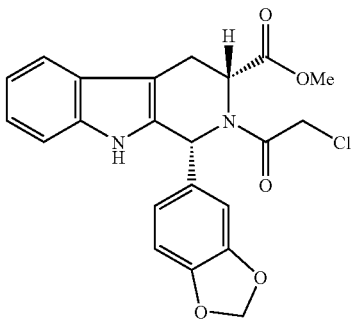

The substituted tetrahydro-β-carboline hydrochloride (II) (83.7 kg, 216 mol) was suspended in THF (335 L) and deionized water (84 L), and treated with triethylamine (Et$_3$N) (57.0 kg, 560 mol) at 0° C. to 20° C. under an N$_2$ atmosphere. Chloroacetyl chloride (ClCH$_2$C(O)Cl) (34.2 kg, 300 mol) in dry THF, (0.6 volumes) then was added at a rate to maintain the temperature at 0° C. to 10° C., followed by stirring the reaction mixture for two hours. The reaction was monitored by HPLC for a Compound (II) content of 4%, by weight, or less. After the acylation reaction was completed, the reaction mixture was subjected to distillation, under vacuum at −30° C. to 50° C., to reduce the volume by about 30%. Then, water (84 L) and isopropyl alcohol (335 L) were added, and the reaction mixture was distilled a second time under reduced pressure at 30° C. to 50° C. to remove about 20% of the volume. The reaction mixture then was cooled to 20° C. to 25° C. and stirred for two hours. The reaction product crystallized, and was filtered and washed with isopropyl alcohol. The reaction product was dried under vacuum at 80° C. to yield 86.7 kg (95%) of chloroacetyl carboline cis-1-(1,3-benzodioxol-5-yl)-2,3,4,9-tetrahydro-1H-pyrido[3,4-b]indole-3-carboxylic acid methyl ester. $^1$H NMR (400 MHz DMSO) δ: 10.86 (1H, s), 7.54 (1H, d, J=7.4), 7.27 (1H, d, J=8.0), 7.11-6.99 (2H, m), δ 6.81-6.75 (2H, m), 6.63 (1H, s), 6.45 (1H, d, J=8.2), 5.97 (2H, d, J=5.8), 5.19 (1H, d, J=6.6), 4.83 (1H, d, J=14), 4.43 (1H, d, J=14), 3.45 (1H, d, J=16), 3.10-3.03 (4H, m).

Alternative solvents for Step 3 include low molecular weight alcohols, such as isopropyl alcohol or n-propyl alcohol; acetone; and methylene chloride.

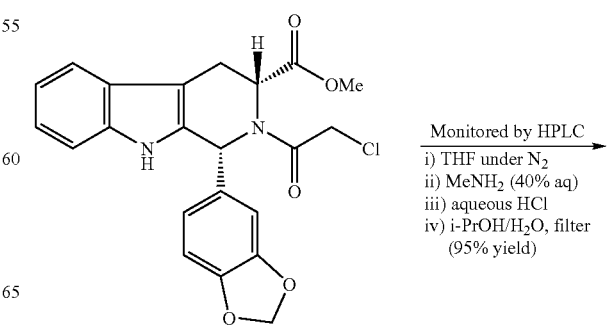

Monitored by HPLC
i) THF under N$_2$
ii) MeNH$_2$ (40% aq)
iii) aqueous HCl
iv) i-PrOH/H$_2$O, filter
(95% yield)

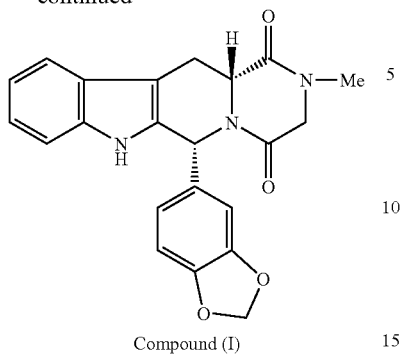
Compound (I)

The chloroacetyl carboline (86.0 kg, 201 mol) was added to THF (430 L), and the resulting mixture was heated to 30° C. to 55° C. under an $N_2$ atmosphere and stirred. The resulting solution then was filtered at a temperature of −45° C. to 50° C. to remove undissolved particles. Methylamine (78.2 kg, 1000 mol) then was added to the solution at a temperature of 5° C. to 25° C. The resulting mixture was stirred at a temperature of 30° C. to 55° C. for about 1 hour, or until HPLC analysis indicated a complete reaction, i.e., less than 1% of the chloroacetyl carboline remained. The mixture was cooled to 0° C. to 30° C., isopropyl alcohol (344 L) and water (175 L) then were added, followed by 12M hydrochloric acid (67 L) to neutralize the excess methylamine, i.e., to pH 2 to 9.4. Upon essentially complete removal of THF by distillation, the solution was treated with isopropyl alcohol (260 L) and water (75 L) and cooled to −5° C. to 30° C., followed by stirring for two hours to crystallize the product. The product was filtered and washed with cold (0° C. to 5° C.) 50% aqueous isopropyl alcohol. The wash solvent was filtered at −5° C. to 30° C., and the product was dried under vacuum at 80° C. or less (e.g., 70° C. to 80° C.) to yield 75 kg (94.6%) of Compound (I). For increased purity, Compound (I) optionally can be recrystallized from acetic acid.

A reference standard was prepared in the same manner, with additional purification by double recrystallization from glacial acetic acid (HOAc). Compound (I) was dissolved in 13 volumes of HOAc at 80° C., and the solution was concentrated to one-third original volume and then cooled to ambient temperature. The product was filtered; washed with MTBE, and dried in vacuum at 80° C. $^1$H NMR (400 MHz, DMSO) δ: 11.0 (1H, s), 7.52 (1H, d, J=7.3 Hz), 7.28 (1H, d, 7.9 Hz), 7.28 (1H, d, J=7.9 Hz), 7.06-6.98 (2H, m), 6.85 (1H, s), 6.76 (2H, s), 6.11 (1H, s), 5.91 (2H, s), 4.40-4.35 (1H, dd, J=4.27, 11.6 Hz), 4.17 (1H, d, J=17.1 Hz), 3.93 (1H, d; J=17.1), 3.54-3.47 (1H, dd, J=4.6, 11.3 Hz), 3.32 (1H, s), 3.00-2.91 (4H, m). HPLC Details: Column: Zorbax SB-Phenyl, 4.6 mm i.d.×25 mm; 2.5 μm particles; Mobile Phase: acetonitrile, 0.1% TFA in water; Flow rate=1.0 mL/min.; Detector wavelength=285 nm; Injection volume=20 μL; Column temperature=ambient; and Retention time=9.0 min.

Obviously, many modifications and variations of the invention as set forth above can be made without departing from the spirit and scope thereof, and, therefore, only such limitations should be imposed as are indicated by the appended claims.

What is claimed is:

1. A method of preparing a compound having a structural formula:

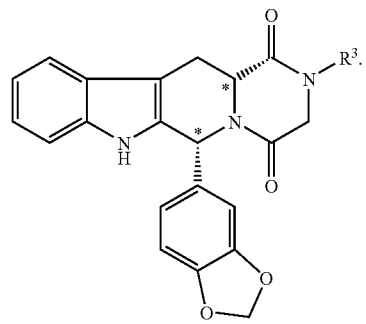

comprising the steps of:
(a) esterifying D-tryptophan in methanol and thionyl chloride to provide D-tryptophan methyl ester hydrochloride;
(b) reacting the D-tryptophan methyl ester hydrochloride with piperonal in refluxing isopropyl alcohol to provide cis-1-(1,3-benzodioxol-5-yl)-2,3,4,9-tetrahydro-1H-pyrido[3,4-b]indole-3-carboxylic acid methyl ester;
(c) reacting the product of step (b) with chloroacetyl chloride and triethylamine to provide (6R, 12aR)-2,3,6,7,12,12a-hexahydro-6-(3,4-methylenedioxyphenyl)-pyrazino-[2',1':6,1]pyrido[3,4-b]indole-1,4'dione

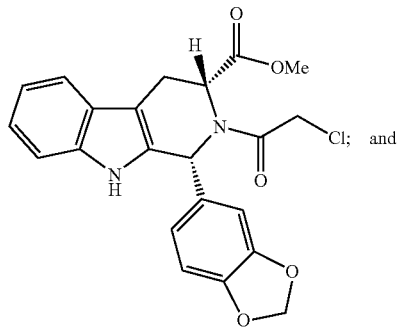

(d) reacting the product of step (c) with methylamine to provide the compound.

2. The method of claim 1 wherein step (d) is performed in tetrahydrofuran, and wherein the tetrahydrofuran is removed and replaced with an alcohol for isolation and purification of the compound.

3. The method of claim 1 wherein the compound is purified by recrystallization from glacial acetic acid.

4. The method of claim 2 wherein the compound is purified by recrystallization from glacial acetic acid.

5. The method of claim 1 wherein the cis-1-(1,3-benzodioxol-5-yl)-2,3,4,9-tetrahydro-1H-pyrido[3,4-b]indole-3-carboxylic acid methyl ester of step (b) is isolated in greater than 90% yield.

* * * * *